United States Patent [19]

Wakiyama et al.

[11] Patent Number: 5,423,514
[45] Date of Patent: Jun. 13, 1995

[54] ALIGNMENT ASSEMBLY FOR ALIGNING A SPRING ELEMENT WITH A LASER BEAM IN A PROBE MICROSCOPE

[75] Inventors: Shigeru Wakiyama; Hiroyoshi Yamamoto; Masatoshi Yasutake, all of Tokyo, Japan

[73] Assignee: Seiko Instruments Inc., Tokyo, Japan

[21] Appl. No.: 217,747

[22] Filed: Mar. 25, 1994

[30] Foreign Application Priority Data

Mar. 25, 1993 [JP] Japan .................. 5-067130

[51] Int. Cl.⁶ ............................................ G01N 21/86
[52] U.S. Cl. ........................................ 250/561; 73/105
[58] Field of Search ................ 250/561, 306, 307; 73/105; 324/757, 762

[56] References Cited

U.S. PATENT DOCUMENTS 5,286,977  2/1994  Yokoyama et al. .................. 73/105
5,296,704  3/1994  Mishima et al. .................... 250/307

*Primary Examiner*—David C. Nelms
*Assistant Examiner*—Que T. Le
*Attorney, Agent, or Firm*—Spensley Horn Jubas & Lubitz

[57] ABSTRACT

A probe microscope has a displacement detecting system formed of a spring element and a photodetecting element, the system being attached to a fine movement element, and a holder, which attached to the spring element fixed to the photodetecting system by a magnetic force, is moved by an alignment jig removably mounted on a sample moving stage in a three-dimensional fashion and a laser beam is converged on a selected point of the spring element with ease while confirming the state of alignment of the spring element with laser light based on an image produced by a camera and displayed on a monitor.

2 Claims, 8 Drawing Sheets

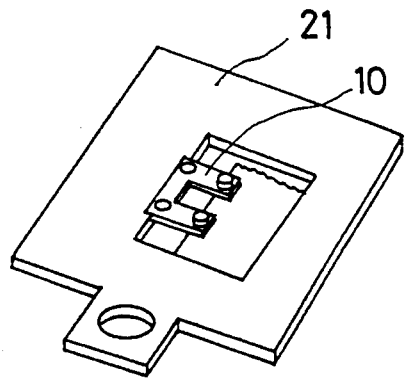
F I G. 4
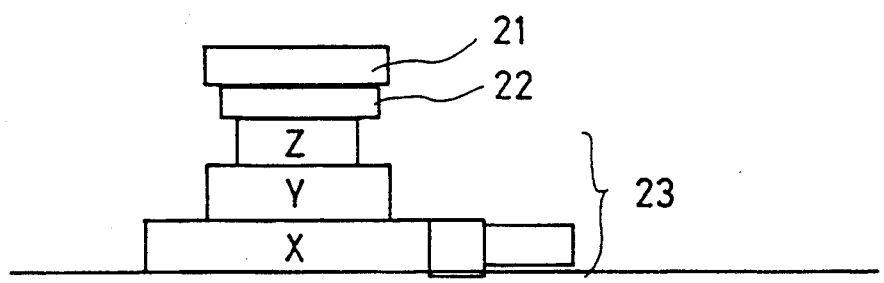
F I G. 5
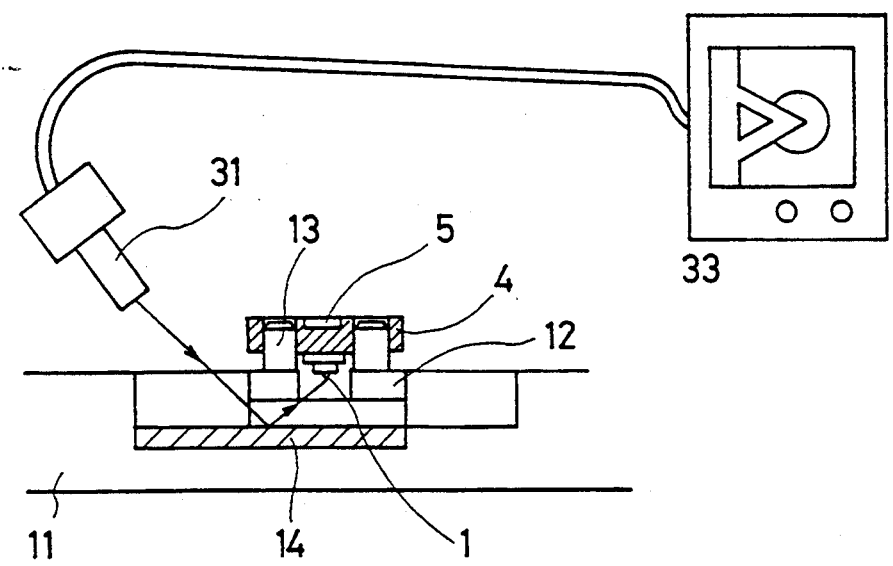
F I G. 6

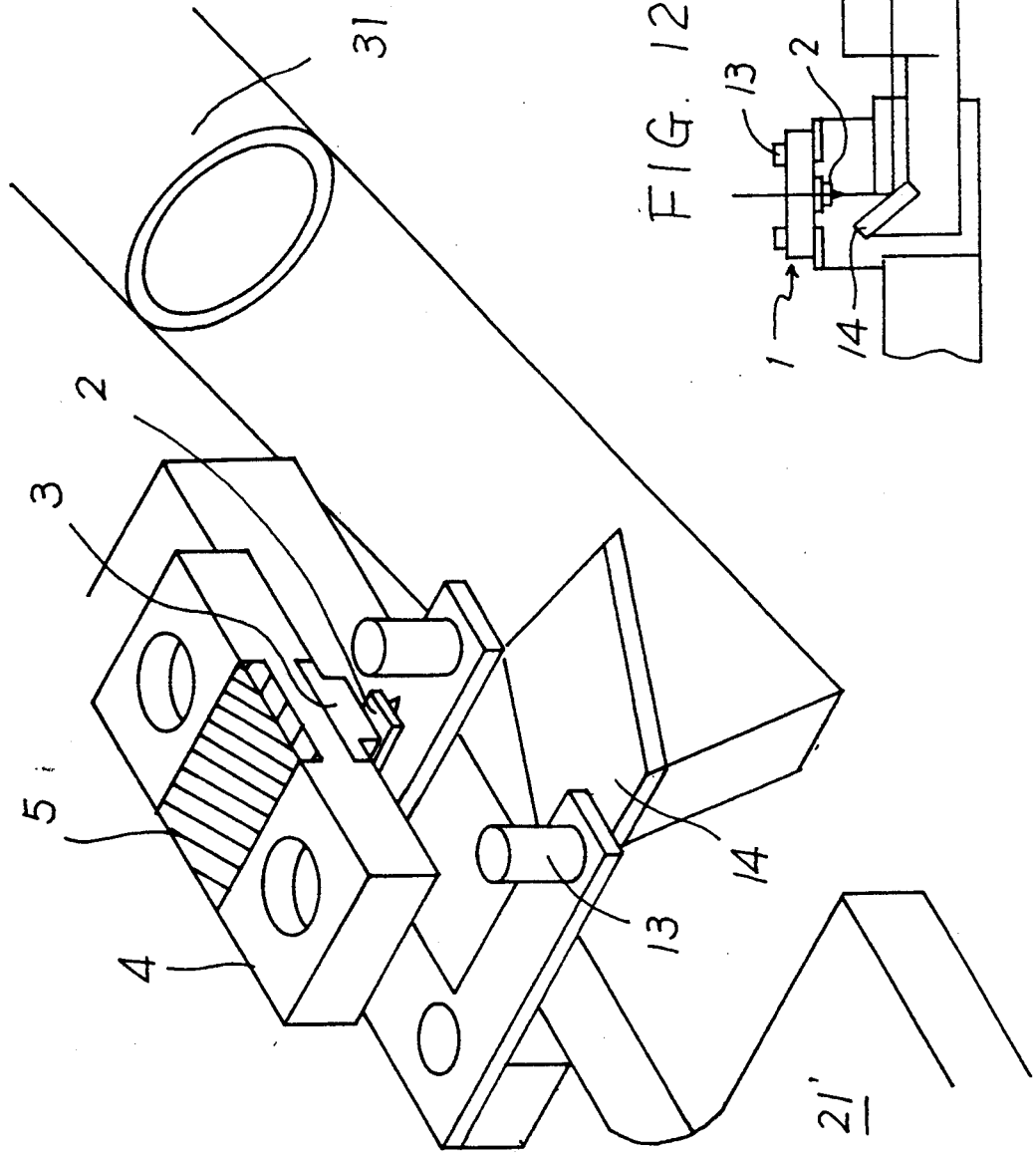
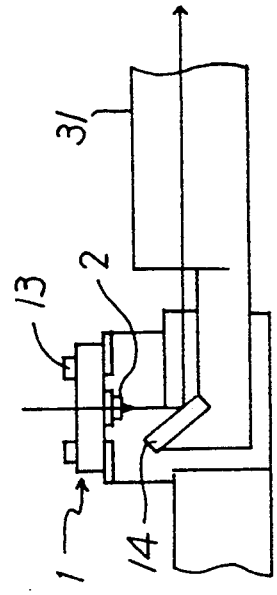
FIG. 12A
FIG. 12B

ALIGNMENT ASSEMBLY FOR ALIGNING A SPRING ELEMENT WITH A LASER BEAM IN A PROBE MICROSCOPE

BACKGROUND OF THE INVENTION

The present invention relates to a probe microscope such as an interatomic force microscope or magnetic force microscope of the type in which various kinds of forces, such as an interatomic force acting between substances, is converted into a displacement by means of a minute spring element and the displacement is detected by a photo-detector in that laser light is applied on the spring element and if there is any positional deviation of light reflected from the spring element, such positional deviation is indicative of the displacement, thereby producing a control signal.

The atomic force microscope as one kind of probe microscope has been expected to be a means for observing the surface configuration of a novel insulating substance and has now been studied since it was invented by G. Binnig as an inventor of STM (refer to Physical Review Letters vol. 56 p. 930, 1986). The principle of this microscope resides in that the interatomic force acting between a detecting chip having its top end sufficiently sharpened and a sample is measured as a displacement of a spring element attached with a detecting probe, the surface of the sample is scanned while the amount of displacement of the spring element is kept constant and the surface configuration of the sample is measured with a control signal for keeping constant the amount of displacement of the spring element serving as configuration information.

The spring element displacement detecting means is roughly classified into a STM system using a tunnel current and an optical system.

The STM system makes use of a so-called tunnel phenomenon, i.e. when a voltage is applied between two conductors which are held close to each other, leaving therebetween a distance in the range between several nanometers and several angstroms, a current begins to flow through the conductors. According to this system, the spring element is made conductive in advance, and a sharp metallurgical probe is caused to come as close as about 1 nanometer to the spring element and a tunneling current is made to flow through the spring element so that the resultant current value is used as a signal indicative of the displacement of the spring element.

As to the optical system, an example using a so-called interference method (refer to Journal of Vacuum Science Technology AG(2) p. 266 Mar./Apr. 1988) and an optical lever type probe microscope (Journal of Applied physics 65(1) p. 164 January 1989) are known. The optical lever type probe microscope utilizes an electric signal converted from an optical signal detected by an optical detecting element, the optical detecting element detecting a deviation of light reflected from a spring element irradiated with laser light, the deviation being due to the probe displacement.

The probe microscope to which the present invention relates is known as an optical lever type. The probe microscope is called an interatomic force microscope if it is of the type in which the probe arranged opposite to the sample is subject to an interatomic force from the latter while it is called a magnetic force microscope if it is subject to a magnetic force from the sample. Thus, it becomes possible to observe the state of the sample by detecting various kinds of forces emanating from, or associated with, the sample.

One known probe microscope is illustrated in FIG. 8. In this microscope, light emanating from a semiconductor laser 106 supplied with a signal from a laser driver 118 is focussed, or concentrated, on the rear surface of a spring element 2 through a lens 108 and the light reflected from the element 2 is focussed, or concentrated, on an optical detecting element 111 through a lens 109. When, for example, a two-element type photodetector is used as element 111, if the photo-detector is so adjusted that light is incident uniformly upon the two pre-separated elements and the signal from each element is supplied to one input of a differential amplifier 19, so that a differential signal is received by differential amplifier 19, it is possible to observe displacement of the spring element 2 attached to a probe 102. The differential signal is supplied to a servo system 120 and in response thereto, a fine movement element 104 carrying sample 101 is driven in the z-direction, which is the vertical direction in FIG. 8. Then the drive signal in the z-direction is supplied to a computer 121 to produce an indication of the surface configuration of the sample.

However, in the case of the above-mentioned optical lever type interatomic microscope, since it drives the sample 101 by the fine movement element 104 fixed to a coarse movement mechanism 105, it has been usual that an attempt to observe a large sample results in lowering the resonance frequency of the fine movement element and so the observation becomes difficult. Further, where the fine movement element is or includes a piezoelectric element, since the diameter thereof is as small as about 30 mm. at the maximum, it is physically difficult to set up the sample. For example, in order to observe a semiconductor wafer or optical disk plate, it has been necessary to divide the sample, with the drawback that the advantage of nondestructive observation capability of the interatomic microscope cannot be fully utilized.

Further, the above-mentioned system has had the problem that since the sample 101 is driven by the fine movement element 104, the load mass on the element 104 fluctuates every measurement time so that the control characteristic and the measuring speed can not be kept constant.

Therefore, as shown in FIG. 9, a displacement detecting system formed of the spring element 2 and the photo-detecting element 111 is attached to the bottom of a fine movement element 104 and the sample 101 is fixed to the coarse movement mechanism 105. Further, in order to reduce the mass load on the fine movement element 104, the semiconductor laser 106 is arranged within a frame 114 and laser light is guided from a location above the fine movement element by means of an optical fiber 107. The spring element 2 is held against a support member 112 by means of a spring 113 and held stationary at a certain angle of inclination with respect to the optical axis of the lens 108. Light from the optical fiber 107 is converged on the top end of the spring element 2 through the lens 108 and light reflected from spring element becomes incident upon the two-element photodetecting element 111. Adjacent to the slight motion element there is provided a metallurgical microscope 115.

The coarse-moving mechanism 105 comprises a three axis stage for movement in x, y and z coordinate directions and the sample 101 is transferred between the metallurgical microscope 115 and the interatomic microscope. Thus there exists an interatomic microscope having the structure that a sample is coarsely observed in advance with a metallurgical microscope and then a part of the sample which is desired to be observed in more detail is observed with the interatomic microscope.

However, in the case of the interatomic microscope of the above-described structure, due to the fact that the displacement detecting system formed of the spring element 2, photodetecting element 111, etc., has its top end attached to the fine movement element, it is difficult to provide an alignment mechanism for converging a semiconductor laser beam on the top end of the spring element 2 because by so doing the weight supported by the fine movement mechanism increases. Therefore, it is not easy to align a laser beam with the top end of the spring element 2, which has a size of several of tens of $\mu$.

SUMMARY OF THE INVENTION

It is an object of the present invention to provide a probe microscope such as an interatomic microscope or magnetic force microscope including a fine movement element and a displacement detecting system formed of a spring element and a photo-detecting element and attached to the fine movement element, and more particularly to provide such type of probe microscope that is provided with means for aligning and converging with ease the semiconductor laser light with, and on, the top end of the spring element.

The probe microscope according to the present invention is constructed such that a displacement detecting system formed of a spring element and a photodetecting element is attached to the fine movement element and the feature of the invention resides in that a holder attached with the spring element fixed to the photodetecting system due to a magnetic force is moved by an alignment jig removably mounted on means, such as a stage, for moving a sample in a three-dimensional fashion and in this case, the laser light is converged on the top end of the spring element with ease while confirming the state of alignment of the spring element with laser light displayed on a monitor through a camera.

According to the present invention, alignment of laser light with the top end of the spring element 2 can be made by the provision of the above-mentioned means without the necessity of providing any additional alignment mechanism, by using a moving means, or stage, prepared for moving a sample accurately. Further, since the alignment jig can be mounted on, and removed from, the moving means with ease, there is no limitation on the mounting area of the sample.

BRIEF DESCRIPTION OF THE DRAWING

FIG. 4 is a perspective view of a cassette block fixed to the alignment jig of FIG. 3.

FIG. 5 is a side elevational view of the cassette block of FIG. 4 mounted to an alignment means, or stage.

FIG. 6 is a pictorial view, partly in cross section, illustrating a means for observing the alignment state of the spring means and laser light according to one embodiment of the present invention.

FIG. 12A is a perspective view of an embodiment of an alignment assembly according to the invention.

FIG. 12B is an elevational detail view of components of the alignment assembly of FIG. 12A.

DESCRIPTION OF THE PREFERRED EMBODIMENTS

One embodiment of the present invention will now be described by referring to the accompanying drawings.

Figure 1:
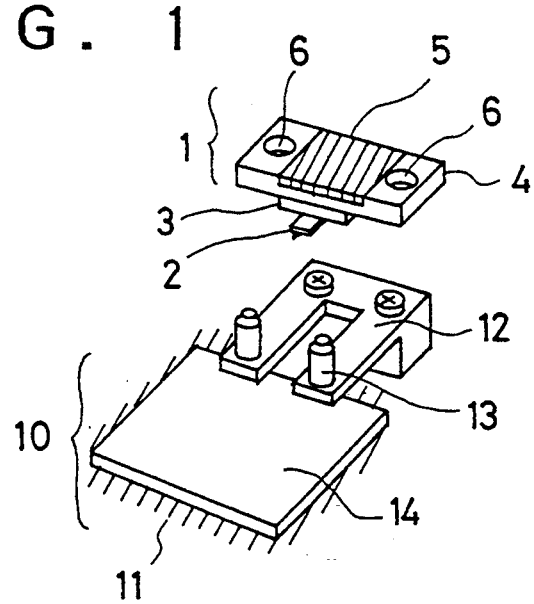
FIG. 1 is a perspective view of portions of a probe microscope according to one embodiment of the present invention, the view especially showing a holder fixed with a spring element and an alignment jig.
Figure 2:
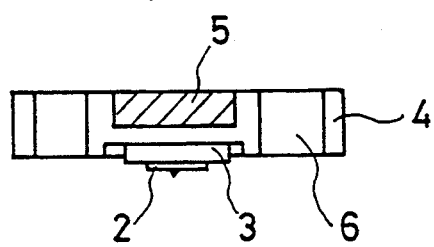
FIG. 2 is a cross-sectional view of the holder of FIG. 1.
Figure 3:
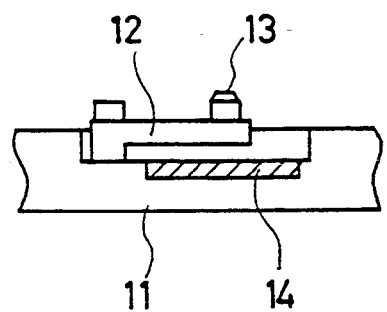
FIG. 3 is a cross-sectional view of the alignment jig of FIG. 1.

FIG. 1 is an exploded perspective view of components of a probe microscope according to the present invention, with the view particularly showing a holder 1 to which a spring element 2 is attached and an alignment jig 10. FIGS. 2 and 3 are cross-sectional views of, respectively, the holder 1 and the alignment jig 10.

The holder 1 includes a base plate 3 made of a magnetic material to which a connection end of spring element 2 is bonded. Holder 1 further includes a base 4 to which a magnet 5 is fixed. Magnet 5 produces a magnetic force which holds base plate 3 in position on base 4. The spring element 2 may also be fixed directly to the base 4 with an adhesive without using the plate 3. However, it may be difficult to fix the spring element 2 to the center of the base 4 in this manner because the element 2 is comparatively small. Therefore, if the spring element 2 is held stationary in a coarsely aligned state, since the fixation is made by a magnetic force, easy repositioning of the spring element becomes possible and further, if the spring element 2 is bonded to the plate 3 with a soluble bonding material, the plate 3 can be reused. Further, the base 4 is provided with alignment holes 6.

The alignment jig 10 is constructed as follows. On a base plate 11 there is fixed a cantilever block 12. At the top of the cantilever block 12 there are fixed alignment pins 13. Pin 13 are made smaller than the holes 6 drilled in the base 4. Further, by making the lever block 12 and the pin 13 of soft, or elastic, material, it is possible to damp impacts occurring at the time of alignment work. A mirror 14 is fixed on base plate 11 for observing the alignment condition of the spring element and the laser light.

The above-mentioned alignment jig 10 may be provided as a component of a cassette block 21 as shown in FIG. 4 so that the mounting and dismounting of the cassette block 21 can be easily made via a cassette block fixing plate 22 fixed onto a three-dimensional moving means, or stage, 23, as shown in FIG. 5. Stage 23 is shown to have, at least conceptually, components for effecting movements in the x, y and z directions.

Further, the alignment state of the spring element and laser light can be confirmed with the aid of the above-mentioned mirror 14 as shown in FIG. 6, from the image obtained directly by a CCD camera 31 and displayed on a monitor 33. It is also possible to use an optical microscope in place of camera 31 and monitor 33.

Next, an alignment procedure according to the present invention will be described with reference to FIGS. 7A, 7B, 7C, 7D and 7E. In Step 1, FIG. 7A, the holder 1 to which the spring element 2 is fixed is set on the alignment jig 10, to one side of a displacement detecting section 41. In Step 2, FIG. 7B, the stage 23 is moved in the X-Y plane to be in operative association with section 41. Since the displacement detecting section 41 is stationary, alignment can be easily made by storing the position thereof in a computer in advance. In Step 3, FIG. 7C, when the stage 23 supporting jig 10 is moved in the height direction (z) until it comes to a certain position, the magnet 5 fixed to the holder 1 is attracted to a magnetic member incorporated into the displacement detecting section 41 so that the holder 1 is lifted slightly away from the alignment jig 10, with pins 13 continuing to engage in holes 6. The stage 23 is stopped when the holder is thus lifted from the jig 10. This position may be stored in the computer.

At this point, the pins 13 of the alignment jig 10 do not deviate from the holes 6 of the holder 1. In Step 4, FIG. 7D, the stage 23 is moved in the x-y plane allowing the holder 1 to move in that plane for alignment while confirming the alignment state of the spring element and laser light from the image observed by camera 31 and displayed on monitor 33. In Step 5, FIG. 7E, the stage 23 is lowered to separate the holder 1 from the alignment jig 10.

Figure 9:
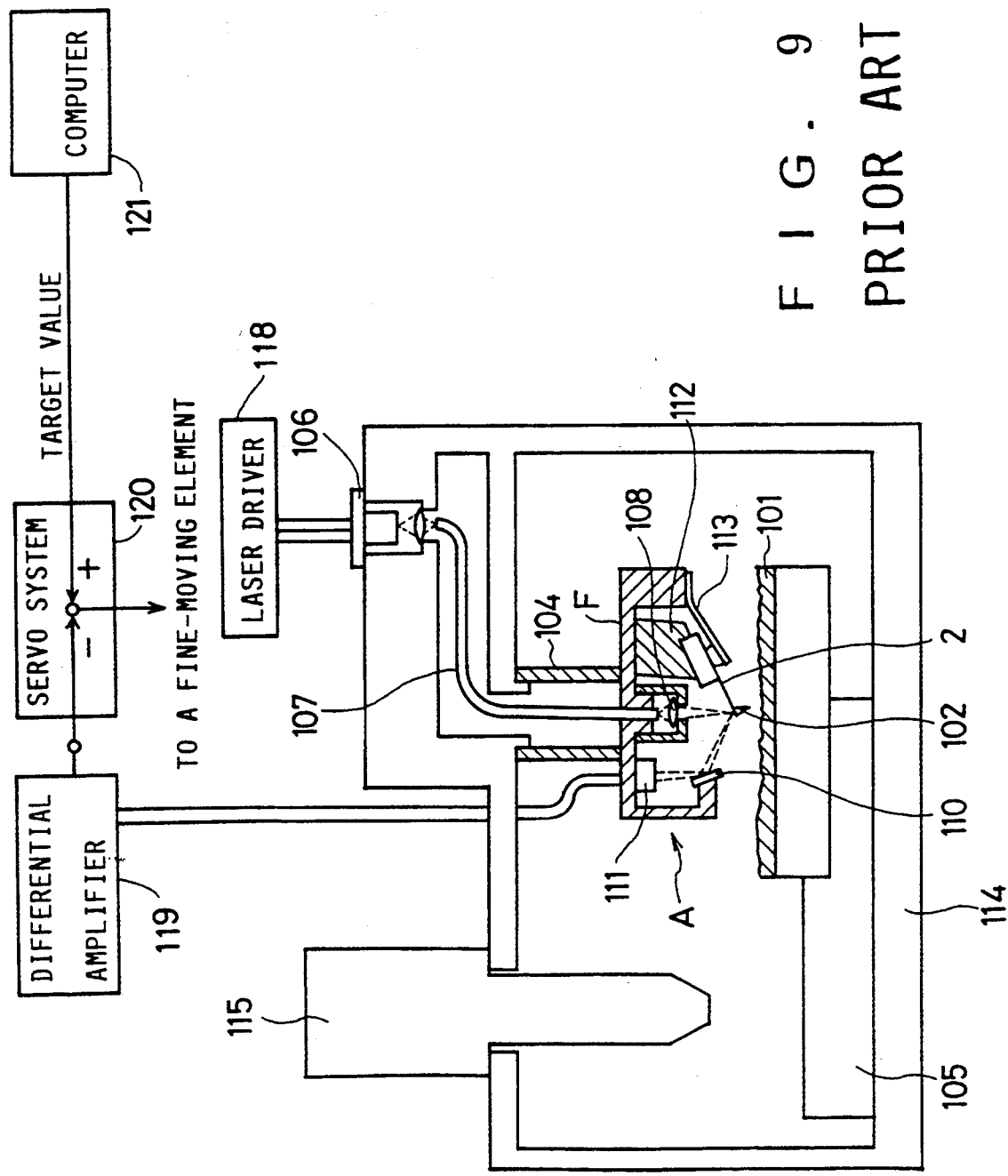
FIG. 9 is a view similar to that of FIG. 8 of another prior art probe microscope.
Figure 10:
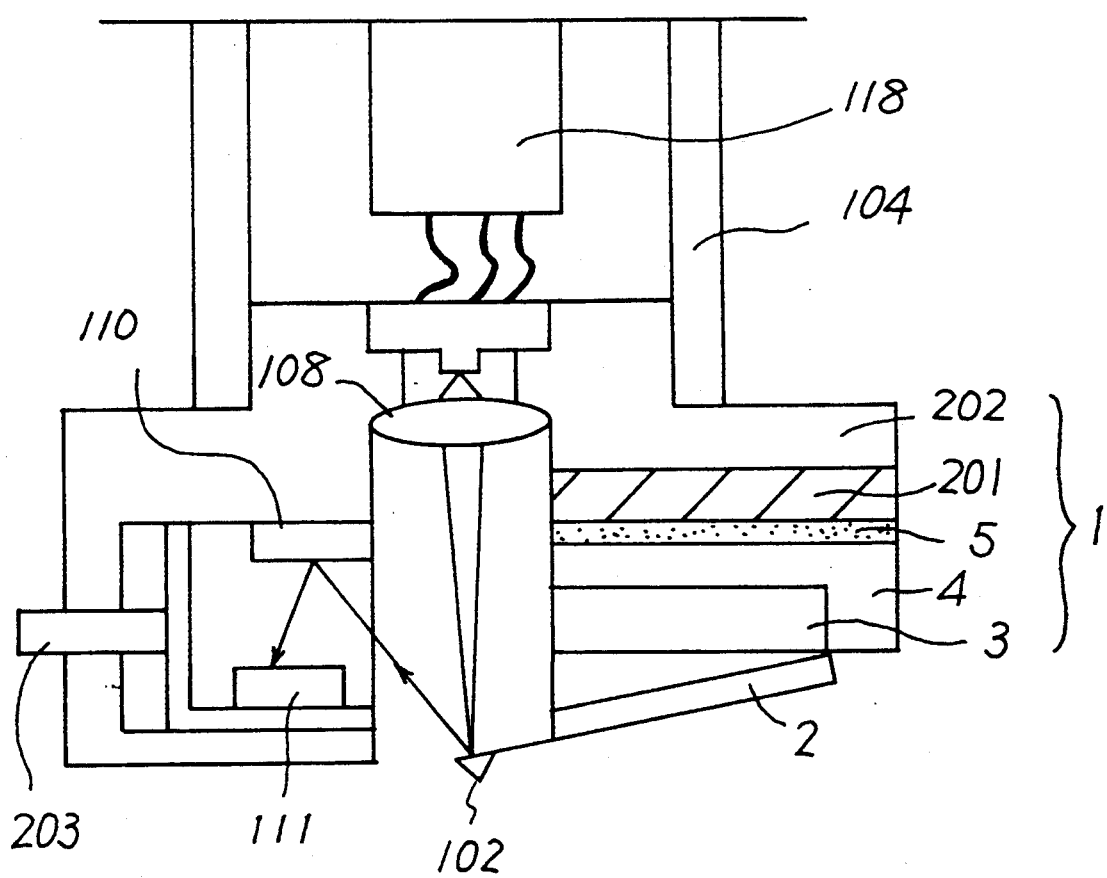
FIG. 10 is an elevational detail view of a portion of a probe microscope having a spring element positioned according to the present invention.

FIG. 10 is an elevational detail view of a portion of a probe microscope, similar to that of FIG. 9, in which probe 102 can be positioned in accordance with the present invention. Parts identical to those of FIG. 9 are identified by the same reference numerals. In FIG. 10, optical fiber 107 is eliminated and the output of laser 106 impinges directly on lens 108. In addition, laser light reflected from spring element 2 is directed to photodetecting element 111 via a mirror 110. The position of element 111 can be adjusted by acting on an adjustment screw 203.

Holder 1, composed of base plate 3, base 4 and magnet 5, is held in place, by magnetic force, on a member 201 made of magnetic material, such as iron. Member 201 is fixed to a housing 202 which is secured, in turn, to the lower end of fine movement element 104. Spring element 2 is secured to plate 3 in a manner to have an inclined, or oblique, orientation relative to the horizontal. Plate 3 is made of a magnetic material, such as iron, and is secured to base 4 by magnetic force. Holder 1 is accurately positioned relative to the laser light beam in the manner described earlier herein.

Figure 11:
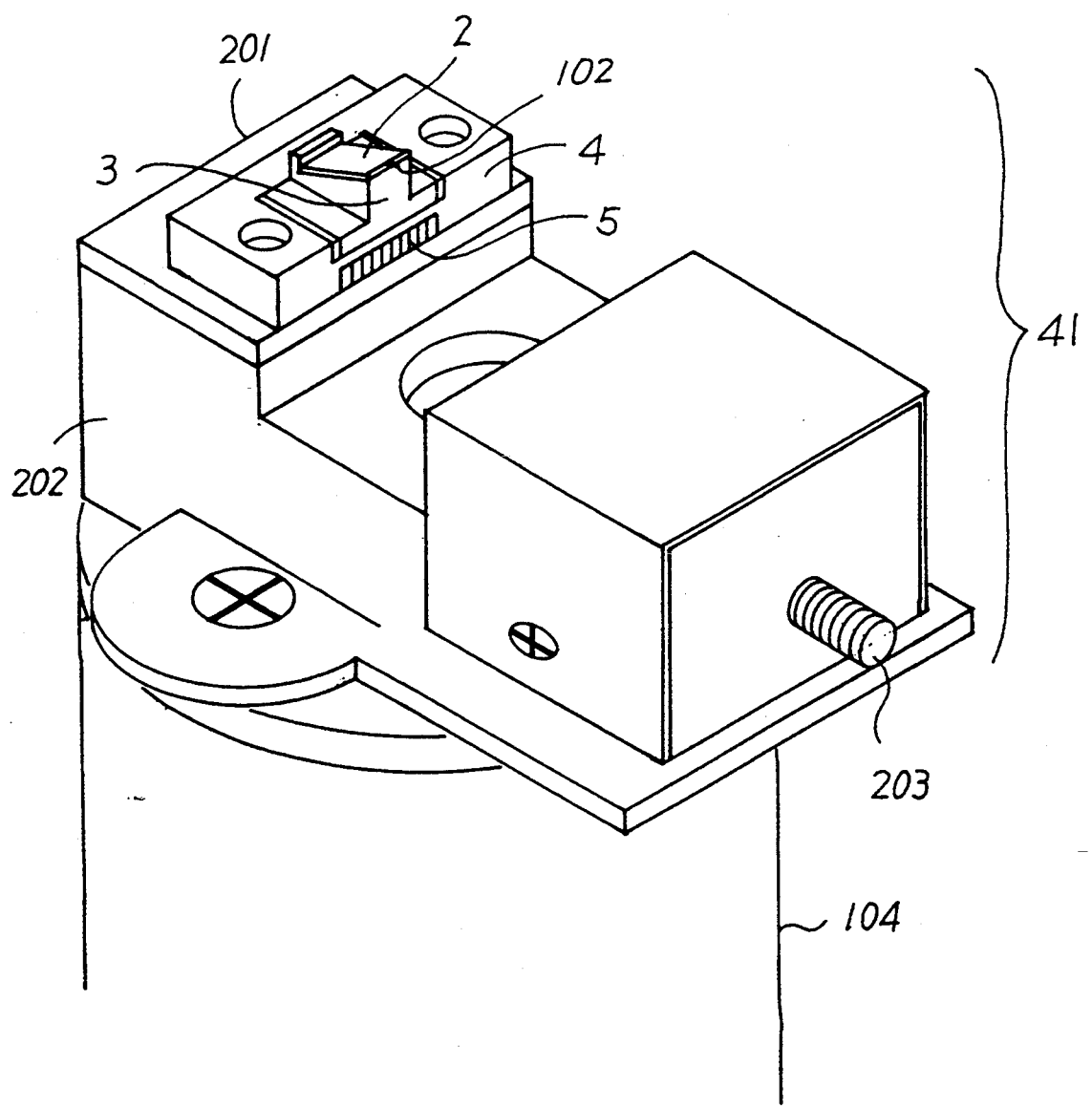
FIG. 11 is a bottom perspective view of the assembly shown in FIG. 10.

FIG. 11 is a bottom perspective view of housing 202 and the components mounted therein. The location of the displacement detecting section, composed essentially of element 111, is indicated at 41. The positioning of holder 1 relative to housing 202 is effected in the manner described above with reference to FIGS. 7A to 7E. When spring element 2 is perfectly aligned with the laser beam, the end of spring element 2 will appear on the monitor display (33 in FIG. 6) to sparkle strongly.

FIGS. 12A and 12B show another embodiment of an alignment assembly according to the invention. Here, the reflecting surface of mirror 14 is oriented at 45° to the horizontal, and camera or microscope 31 has a horizontal optical axis. The laser light beam and an image of the free end of spring element 2 will be reflected by mirror 14 along the optical axis of camera or microscope 31. Cassette block 21' differs in form from block 21 of FIG. 4.

Figure 7A:
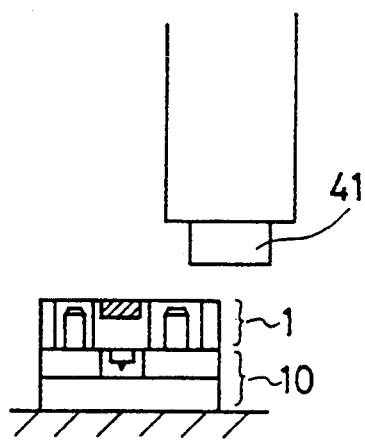
FIGS. 7A, 7B, 7C, 7D and 7E are diagrammatic illustrations of spring element-laser light alignment procedures according to the invention.
Figure 7B:
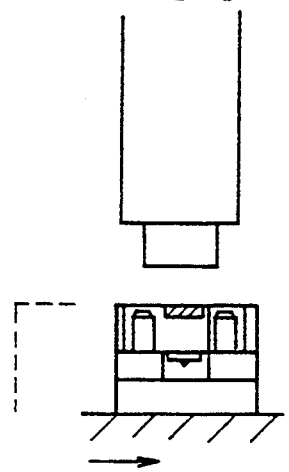
Figure 7C:
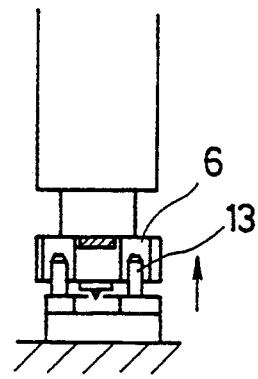
Figure 7D:
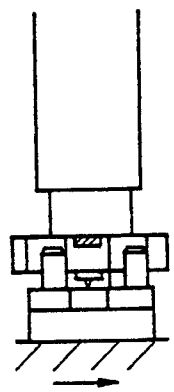
Figure 7E:
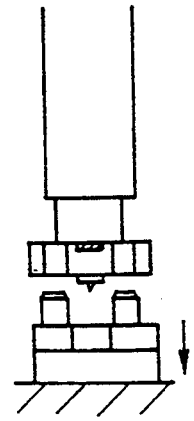
Figure 8:
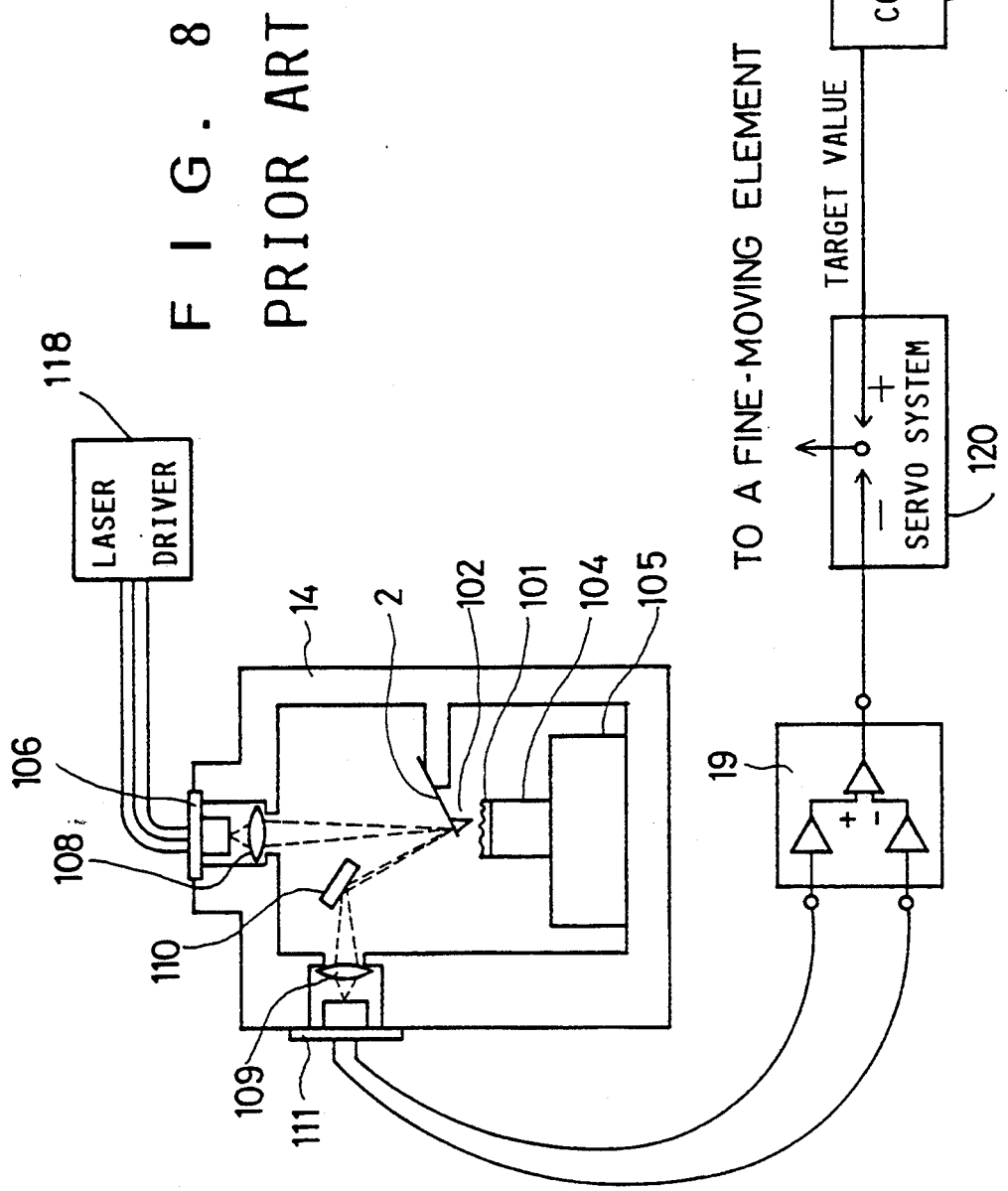
FIG. 8 is partly an elevational, cross-sectional view and partly a block diagram of a prior art probe microscope.

Cassette block 21 is mounted on mechanism 23, as shown in FIG. 4, while housing 202 is fixed to fine movement element 104. Therefore, for properly positioning spring element 2 relative to the laser light beam, cassette block 21 will be moved by mechanism 23 to cause pins 13 to displace holder 1 in the X-Y plane, as depicted in FIG. 7D. When holder 1 has been properly positioned, cassette block 21 is moved downwardly in the Z direction, as depicted in FIG. 7E, leaving holder 1 secured to housing 202 by magnetic force with the free end of spring element 2 correctly aligned with the laser beam. After holder 1 has been correctly positioned, cassette block 21 with jig 10 is removed from the probe.

The present invention has the effect of being able to align laser light with the top end of a spring element of a size of several tens of $\mu$ since the invention makes use of means for moving a sample very accurately.

This application relates to subject matter disclosed in Japanese Application number 5-67130, filed on Mar. 25, 1993, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A method for aligning a spring element with a laser beam in a probe microscope for observing a sample surface, which microscope includes the spring element, for converting an interatomic force or magnetic force from the sample surface into a displacement of the spring, displacement detecting means for detecting displacement of the spring by a photo-detector to which the laser beam is reflected from the spring element by detecting any positional deviation, from a reference position, of light reflected from the spring element, a coarse movement mechanism and a fine movement element for effecting relative movement between the sample and the spring element, control means for keeping constant the distance between the sample and the spring element, a vibration eliminating mechanism for keeping the microscope free of vibration and a computer for controlling the microscope in its entirety, with the spring element and the displacement detecting means being arranged on the side of the fine movement element, said method comprising bringing a selected point of the spring element and the laser beam into alignment with each other by operating the coarse movement mechanism for effecting relative movement between the sample and the spring element with the aid of a jig provided on the coarse movement mechanism.

2. An alignment assembly for aligning a spring element with a laser beam in a probe microscope for observing a sample surface, which microscope includes the spring element, for converting an interatomic force or magnetic force from the sample surface into a displacement of the spring, displacement detecting means for detecting displacement of the spring by a photodetector to which the laser beam is reflected from the spring element by detecting any positional deviation, from a reference position, of light reflected from the spring element, a coarse movement mechanism and a fine movement element for effecting relative movement between the sample and the spring element, control means for keeping constant the distance between the sample and the spring element, a vibration eliminating mechanism for keeping the microscope free of vibration and a computer for controlling the microscope in its entirety, with the spring element and the displacement detecting means being arranged on the side of the fine movement element, wherein said alignment assembly comprises:

a holder assembly including a base provided with alignment holes and having means for holding said spring element by a magnetic force; and an alignment jig including a lever block having a top end provided with pins to fit in said holes of said holder assembly, and a mirror positioned to observe an alignment state of said spring element and said laser beam, alignment of a selected point of said spring element with said laser beam being confirmed by a display on a monitor of an image provided by a camera while moving said holder assembly with said alignment jig by said coarse movement mechanism.

* * * * *